United States Patent
Sandahl

(10) Patent No.: US 9,757,256 B2
(45) Date of Patent: Sep. 12, 2017

(54) PUMP MECHANISM FOR VACUUM SUSPENSION SYSTEM

(71) Applicant: OSSUR HF, Reykjavik (IS)

(72) Inventor: David Sandahl, Reykjavik (IS)

(73) Assignee: OSSUR HF, Reykjavik (IS)

( * ) Notice: Subject to any disclaimer, the term of this patent is extended or adjusted under 35 U.S.C. 154(b) by 0 days.

(21) Appl. No.: 14/747,788

(22) Filed: Jun. 23, 2015

(65) Prior Publication Data
US 2016/0000585 A1    Jan. 7, 2016

Related U.S. Application Data

(60) Provisional application No. 62/019,674, filed on Jul. 1, 2014.

(51) Int. Cl.
*A61F 2/80* (2006.01)
*F04B 45/04* (2006.01)
*F04B 53/10* (2006.01)

(52) U.S. Cl.
CPC ........... *A61F 2/80* (2013.01); *F04B 45/04* (2013.01); *F04B 53/10* (2013.01); *A61F 2002/802* (2013.01); *A61F 2002/805* (2013.01); *A61F 2002/807* (2013.01)

(58) Field of Classification Search
CPC ....... A61F 2002/807; A61F 2/80; F04B 45/04
See application file for complete search history.

(56) References Cited

U.S. PATENT DOCUMENTS

| | | |
|---|---|---|
| 708,685 A | 9/1902 | White |
| 980,457 A | 1/1911 | Toles |
| 1,288,803 A | 12/1918 | Beck |
| 1,586,015 A | 5/1926 | Underwood |
| 2,424,278 A | 7/1947 | Kunkel |
| 2,464,443 A | 3/1949 | Ganoe et al. |
| 2,530,285 A | 11/1950 | Catranis |
| 2,533,404 A | 12/1950 | Sharp et al. |
| 2,606,325 A | 8/1952 | Nielson et al. |

(Continued)

FOREIGN PATENT DOCUMENTS

| | | |
|---|---|---|
| AU | 670631 B2 | 7/1996 |
| BE | 675 386 A | 5/1966 |

(Continued)

OTHER PUBLICATIONS

International Search Report and Written Opinion from corresponding International PCT Application No. PCT/US2014/019218, May 9, 2014.

(Continued)

*Primary Examiner* — Bruce E Snow
*Assistant Examiner* — Melissa Hoban
(74) *Attorney, Agent, or Firm* — Workman Nydegger

(57) ABSTRACT

A vacuum suspension system includes a pump mechanism operatively connectable to a prosthetic socket. The pump mechanism has a first member and a second member. First and second fluid chambers are located between the first and second members. The second fluid chamber is fluidly separate from the first fluid chamber, and arranged for fluid communication with the socket. An increase in volume of the first fluid chamber mechanically expands the second fluid chamber, which, in turn, creates a vacuum pressure in the second fluid chamber.

15 Claims, 6 Drawing Sheets

(56) References Cited

U.S. PATENT DOCUMENTS

| | | |
|---|---|---|
| 2,664,572 A | 1/1954 | Blevens |
| 2,671,225 A | 3/1954 | Schoene et al. |
| 2,696,010 A | 12/1954 | Robinson |
| 2,696,011 A | 12/1954 | Galdik |
| 2,790,180 A | 4/1957 | Hauser |
| 2,808,593 A | 10/1957 | Anderson |
| 3,253,600 A | 5/1966 | Scholl |
| 3,322,873 A | 5/1967 | Hitchcock |
| 3,377,416 A | 4/1968 | Kandel |
| 3,557,387 A | 1/1971 | Ohlenbusch et al. |
| 3,631,542 A | 1/1972 | Potter |
| 3,712,298 A | 1/1973 | Snowdon et al. |
| 3,732,578 A | 5/1973 | Pollack |
| 3,751,733 A | 8/1973 | Fletcher et al. |
| 3,806,958 A | 4/1974 | Gusev |
| 3,858,379 A | 1/1975 | Graves et al. |
| 3,889,301 A | 6/1975 | Bonner, Sr. |
| 3,895,405 A | 7/1975 | Edwards |
| 3,922,727 A | 12/1975 | Bianco |
| 3,975,350 A | 8/1976 | Hudgin et al. |
| 3,991,424 A | 11/1976 | Prahl |
| 4,010,052 A | 3/1977 | Edwards |
| 4,106,745 A | 8/1978 | Carrow |
| 4,133,776 A | 1/1979 | Pruett et al. |
| 4,282,325 A | 8/1981 | Rubenstein et al. |
| 4,283,800 A | 8/1981 | Wilson |
| 4,314,398 A | 2/1982 | Pettersson |
| 4,381,768 A | 5/1983 | Erichsen et al. |
| 4,404,296 A | 9/1983 | Schapel |
| 4,456,642 A | 6/1984 | Burgdorfer et al. |
| 4,466,936 A | 8/1984 | Schapel |
| 4,479,272 A | 10/1984 | Beldzidsky |
| 4,623,354 A | 11/1986 | Childress et al. |
| 4,634,446 A | 1/1987 | Kristinsson |
| 4,635,626 A | 1/1987 | Lerman |
| 4,655,779 A | 4/1987 | Janowiak |
| 4,704,129 A | 11/1987 | Massey |
| 4,822,371 A | 4/1989 | Jolly et al. |
| 4,828,325 A | 5/1989 | Brooks |
| 4,888,829 A | 12/1989 | Kleinerman et al. |
| 4,908,037 A | 3/1990 | Ross |
| 4,923,475 A | 5/1990 | Gosthnian et al. |
| 5,007,937 A | 4/1991 | Fishman et al. |
| 5,108,455 A | 4/1992 | Telikicherla |
| 5,108,456 A | 4/1992 | Coonan, III |
| 5,133,776 A | 7/1992 | Crowder |
| 5,139,523 A | 8/1992 | Paton et al. |
| 5,163,965 A | 11/1992 | Rasmusson et al. |
| 5,201,774 A | 4/1993 | Greene |
| 5,211,667 A | 5/1993 | Danforth |
| 5,221,222 A | 6/1993 | Townes |
| 5,258,037 A | 11/1993 | Caspers |
| 5,314,497 A * | 5/1994 | Fay ............... A61F 2/7843 623/33 |
| 5,353,525 A | 10/1994 | Grim |
| 5,362,834 A | 11/1994 | Schapel et al. |
| 5,376,129 A | 12/1994 | Faulkner et al. |
| 5,376,131 A | 12/1994 | Lenze et al. |
| 5,376,132 A | 12/1994 | Caspers |
| 5,397,628 A | 3/1995 | Crawley et al. |
| 5,405,407 A | 4/1995 | Kodama et al. |
| 5,480,455 A | 1/1996 | Norvell |
| 5,490,537 A | 2/1996 | Hill |
| 5,507,834 A | 4/1996 | Laghi |
| 5,534,034 A | 7/1996 | Caspers |
| 5,549,709 A | 8/1996 | Caspers |
| 5,555,216 A | 9/1996 | Drouot |
| 5,571,208 A | 11/1996 | Caspers |
| 5,593,454 A | 1/1997 | Helmy |
| D379,845 S | 6/1997 | Lee |
| 5,658,353 A | 8/1997 | Layton |
| 5,658,354 A | 8/1997 | Norvell |
| 5,702,488 A | 12/1997 | Wood et al. |
| 5,702,489 A | 12/1997 | Slemker |
| 5,709,017 A | 1/1998 | Hill |
| 5,728,166 A | 3/1998 | Slemker |
| 5,728,167 A | 3/1998 | Lohmann |
| 5,728,168 A | 3/1998 | Laghi et al. |
| 5,728,169 A | 3/1998 | Norvell |
| 5,728,170 A | 3/1998 | Becker et al. |
| 5,732,578 A | 3/1998 | Kang |
| 5,735,906 A | 4/1998 | Caspers |
| 5,807,303 A | 9/1998 | Bays |
| 5,830,237 A | 11/1998 | Kania |
| 5,846,063 A | 12/1998 | Lakic |
| 5,885,509 A | 3/1999 | Kristinsson |
| 5,888,216 A | 3/1999 | Haberman |
| 5,888,230 A * | 3/1999 | Helmy ............... A61F 2/7812 602/62 |
| 5,888,231 A | 3/1999 | Sandvig et al. |
| 5,904,721 A | 5/1999 | Henry et al. |
| 5,904,722 A | 5/1999 | Caspers |
| 5,931,872 A | 8/1999 | Lohmann |
| 5,944,760 A | 8/1999 | Christensen |
| 5,980,577 A | 11/1999 | Radis et al. |
| 5,984,972 A | 11/1999 | Huston et al. |
| 6,007,582 A | 12/1999 | May |
| 6,063,125 A | 5/2000 | Arbogast et al. |
| 6,066,107 A | 5/2000 | Habermeyer |
| D429,335 S | 8/2000 | Caspers et al. |
| 6,117,117 A | 9/2000 | Mauch |
| 6,136,039 A | 10/2000 | Kristinsson et al. |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,296,669 B1 | 10/2001 | Thorn et al. |
| 6,334,876 B1 | 1/2002 | Perkins |
| 6,361,568 B1 | 3/2002 | Hoerner |
| 6,362,387 B1 | 3/2002 | Carlson et al. |
| 6,402,788 B1 | 6/2002 | Wood et al. |
| 6,406,499 B1 | 6/2002 | Kania |
| 6,478,826 B1 | 11/2002 | Phillips et al. |
| 6,485,776 B2 | 11/2002 | Janusson et al. |
| 6,508,842 B1 | 1/2003 | Caspers |
| 6,544,292 B1 | 4/2003 | Laghi |
| 6,554,868 B1 | 4/2003 | Caspers |
| 6,589,289 B2 | 7/2003 | Ingimarsson |
| 6,602,295 B1 | 8/2003 | Doddroe et al. |
| 6,613,096 B1 | 9/2003 | Shirvis |
| 6,626,952 B2 | 9/2003 | Janusson et al. |
| 6,645,253 B2 * | 11/2003 | Caspers ............... A61F 2/7812 623/26 |
| 6,673,117 B1 | 1/2004 | Soss et al. |
| 6,702,858 B2 | 3/2004 | Christensen |
| 6,706,364 B2 | 3/2004 | Janusson et al. |
| 6,726,726 B2 | 4/2004 | Caspers |
| 6,761,742 B2 | 7/2004 | Caspers |
| 6,767,370 B1 | 7/2004 | Mosler et al. |
| 6,797,008 B1 | 9/2004 | Arbogast et al. |
| D499,794 S | 12/2004 | Comer |
| 6,855,170 B2 | 2/2005 | Gramnas |
| 6,863,695 B2 | 3/2005 | Doddroe et al. |
| 6,926,742 B2 | 8/2005 | Caspers et al. |
| 6,964,688 B1 | 11/2005 | Kania |
| 6,969,408 B2 | 11/2005 | Lecomte et al. |
| 6,974,484 B2 | 12/2005 | Caspers |
| 7,001,563 B2 | 2/2006 | Janusson et al. |
| 7,025,792 B2 | 4/2006 | Collier |
| 7,025,793 B2 | 4/2006 | Egilsson |
| D526,046 S | 8/2006 | Lin |
| 7,105,122 B2 * | 9/2006 | Karason ............... A61F 2/5046 264/314 |
| 7,118,602 B2 | 10/2006 | Bjarnason |
| 7,255,131 B2 | 8/2007 | Paper et al. |
| 7,371,262 B2 | 5/2008 | Lecomte et al. |
| 7,427,297 B2 | 9/2008 | Patterson et al. |
| 7,448,407 B2 | 11/2008 | Alley et al. |
| 7,468,079 B2 | 12/2008 | Collier |
| 7,686,848 B2 | 3/2010 | Christensen |
| 7,744,653 B2 | 6/2010 | Rush et al. |
| D634,813 S | 3/2011 | Hernandez, IV |
| 7,909,884 B2 | 3/2011 | Egilsson et al. |

(56) References Cited

U.S. PATENT DOCUMENTS

| | | | |
|---|---|---|---|
| 7,922,775 B2 | 4/2011 | Caspers | |
| 7,947,085 B2 | 5/2011 | Haines et al. | |
| D639,825 S | 6/2011 | Murakami et al. | |
| 7,993,413 B2 | 8/2011 | Perkins et al. | |
| 8,007,543 B2 | 8/2011 | Martin | |
| 8,034,120 B2 | 10/2011 | Egilsson et al. | |
| 8,052,760 B2 | 11/2011 | Egilsson et al. | |
| 8,080,065 B2 * | 12/2011 | Scussel | A61F 2/7812 623/32 |
| 8,097,043 B2 | 1/2012 | Egilsson | |
| 8,097,766 B2 | 1/2012 | Carlson et al. | |
| 8,114,167 B2 | 2/2012 | Caspers | |
| D655,393 S | 3/2012 | Whitaker | |
| D656,223 S | 3/2012 | Cronje et al. | |
| 8,298,294 B2 | 10/2012 | Kaltenborn et al. | |
| 8,317,876 B2 | 11/2012 | Mosler | |
| 8,343,233 B2 | 1/2013 | Perkins et al. | |
| D675,714 S | 2/2013 | Nguyen | |
| D681,782 S | 5/2013 | Bohm et al. | |
| 8,523,951 B2 | 9/2013 | Kania | |
| D691,240 S | 10/2013 | Iranyi et al. | |
| D691,701 S | 10/2013 | Iranyi et al. | |
| D691,702 S | 10/2013 | Iranyi et al. | |
| D691,703 S | 10/2013 | Iranyi et al. | |
| D702,320 S | 4/2014 | Pifer | |
| 8,911,506 B2 | 12/2014 | Egilsson et al. | |
| 8,956,422 B2 | 2/2015 | Halldorsson | |
| 8,961,618 B2 | 2/2015 | Lecomte et al. | |
| 9,044,348 B2 | 6/2015 | Halldorsson et al. | |
| 9,056,022 B2 | 6/2015 | Egilsson et al. | |
| 9,060,885 B2 | 6/2015 | Egilsson et al. | |
| 9,066,821 B2 | 6/2015 | Egilsson et al. | |
| 9,066,822 B2 | 6/2015 | Caldwell et al. | |
| 9,072,617 B2 | 7/2015 | Halldorsson et al. | |
| 9,198,790 B2 | 12/2015 | Babkes et al. | |
| 2001/0005798 A1 | 6/2001 | Caspers | |
| 2001/0016781 A1 | 8/2001 | Caspers | |
| 2002/0087215 A1 | 7/2002 | Caspers | |
| 2002/0091449 A1 | 7/2002 | Caspers et al. | |
| 2002/0103545 A1 | 8/2002 | Arbogast et al. | |
| 2002/0128580 A1 | 9/2002 | Carlson et al. | |
| 2003/0191539 A1 | 10/2003 | Caspers | |
| 2004/0024322 A1 | 2/2004 | Caspers | |
| 2004/0030411 A1 | 2/2004 | Caspers | |
| 2004/0064195 A1 | 4/2004 | Herr | |
| 2004/0122528 A1 | 6/2004 | Egilsson | |
| 2004/0163278 A1 | 8/2004 | Caspers et al. | |
| 2004/0181290 A1 | 9/2004 | Caspers | |
| 2004/0236434 A1 | 11/2004 | Carstens | |
| 2004/0260403 A1 | 12/2004 | Patterson et al. | |
| 2005/0131324 A1 | 6/2005 | Bledsoe | |
| 2005/0131549 A1 | 6/2005 | Caspers | |
| 2005/0143838 A1 | 6/2005 | Collier | |
| 2005/0240282 A1 | 10/2005 | Rush et al. | |
| 2005/0267603 A1 | 12/2005 | Lecomte et al. | |
| 2006/0212130 A1 | 9/2006 | Collier | |
| 2006/0212131 A1 | 9/2006 | Curtis | |
| 2006/0224246 A1 | 10/2006 | Clausen et al. | |
| 2007/0005149 A1 | 1/2007 | Egilsson et al. | |
| 2007/0043316 A1 | 2/2007 | Carlson et al. | |
| 2007/0055383 A1 | 3/2007 | King | |
| 2007/0112440 A1 | 5/2007 | Perkins et al. | |
| 2007/0196222 A1 | 8/2007 | Mosler et al. | |
| 2007/0204487 A1 | 9/2007 | Clough | |
| 2008/0086218 A1 | 4/2008 | Egilsson | |
| 2008/0243266 A1 * | 10/2008 | Haynes | A61F 2/68 623/34 |
| 2008/0269911 A1 | 10/2008 | Street et al. | |
| 2008/0269912 A1 | 10/2008 | Gobbers et al. | |
| 2009/0036998 A1 | 2/2009 | Finlinson et al. | |
| 2009/0132056 A1 | 5/2009 | Kania | |
| 2009/0157196 A1 | 6/2009 | Danzig et al. | |
| 2009/0198346 A1 | 8/2009 | Perkins et al. | |
| 2009/0204229 A1 | 8/2009 | Mosler et al. | |
| 2010/0070051 A1 | 3/2010 | Carstens | |
| 2010/0087931 A1 | 4/2010 | Bogue | |
| 2010/0106260 A1 * | 4/2010 | Phillips | A61F 2/602 623/53 |
| 2010/0262261 A1 * | 10/2010 | Laghi | A61F 2/80 623/37 |
| 2010/0312359 A1 | 12/2010 | Caspers | |
| 2010/0312360 A1 * | 12/2010 | Caspers | A61F 2/66 623/34 |
| 2010/0331749 A1 | 12/2010 | Powaser | |
| 2011/0035027 A1 | 2/2011 | McCarthy | |
| 2011/0060421 A1 | 3/2011 | Martin et al. | |
| 2011/0071649 A1 | 3/2011 | McKinney | |
| 2011/0087142 A1 | 4/2011 | Ravikumar et al. | |
| 2011/0130846 A1 | 6/2011 | Kampas et al. | |
| 2011/0202143 A1 | 8/2011 | Caspers | |
| 2011/0270413 A1 | 11/2011 | Haynes | |
| 2011/0295386 A1 | 12/2011 | Perkins et al. | |
| 2012/0000092 A1 | 1/2012 | Ingvarsson et al. | |
| 2012/0035520 A1 | 2/2012 | Imgimundarson et al. | |
| 2012/0123559 A1 | 5/2012 | Mosler et al. | |
| 2012/0173000 A1 | 7/2012 | Caspers | |
| 2012/0173001 A1 | 7/2012 | Caspers | |
| 2012/0191217 A1 | 7/2012 | Mackenzie | |
| 2013/0053982 A1 | 2/2013 | Halldorsson | |
| 2013/0096694 A1 | 4/2013 | Caldwell et al. | |
| 2013/0211544 A1 | 8/2013 | Jonsson et al. | |
| 2013/0282142 A1 | 10/2013 | Perkins et al. | |
| 2013/0289741 A1 * | 10/2013 | Halldorsson | A61F 2/80 623/34 |
| 2014/0243997 A1 | 8/2014 | Clausen et al. | |
| 2014/0249648 A1 * | 9/2014 | Sandahl | A61F 2/80 623/32 |
| 2016/0120665 A1 | 5/2016 | Muller | |

FOREIGN PATENT DOCUMENTS

| | | |
|---|---|---|
| CA | 2 098 945 C | 7/1997 |
| CN | 1946358 A | 4/2007 |
| CN | 1989342 A | 6/2007 |
| CN | 101815870 A | 8/2010 |
| DE | 685 861 C | 12/1939 |
| DE | 745 981 C | 5/1944 |
| DE | 27 12 342 A1 | 9/1977 |
| DE | 27 29 800 A1 | 1/1979 |
| DE | 32 21 920 A1 | 4/1983 |
| DE | 42 17 877 A1 | 12/1992 |
| DE | 43 21 182 C1 | 12/1994 |
| DE | 94 18 210 U1 | 1/1995 |
| DE | 94 19 211 U1 | 2/1995 |
| DE | 94 17 913 U1 | 3/1995 |
| DE | 299 05 020 U1 | 7/1999 |
| DE | 29823435 U1 | 7/1999 |
| EP | 0 019 612 A1 | 11/1980 |
| EP | 0 057 838 A1 | 8/1982 |
| EP | 0 057 839 A1 | 8/1982 |
| EP | 0 086 147 A1 | 8/1983 |
| EP | 0 261 884 A1 | 3/1988 |
| EP | 0 320 170 A1 | 6/1989 |
| EP | 0 363 654 A2 | 4/1990 |
| EP | 0 631 765 A1 | 1/1995 |
| EP | 0 650 708 A1 | 5/1995 |
| EP | 0 870 485 A2 | 10/1998 |
| EP | 1 509 176 A1 | 3/2005 |
| EP | 1 875 881 A1 | 1/2008 |
| EP | 2816978 A1 | 12/2014 |
| FR | 1 135 516 A | 4/1957 |
| FR | 1 532 625 A | 7/1968 |
| FR | 2 420 035 A1 | 10/1979 |
| FR | 2 501 999 A1 | 9/1982 |
| GB | 136 504 A | 12/1919 |
| GB | 267 988 A | 3/1927 |
| GB | 2 069 847 A | 9/1981 |
| GB | 2 149 309 A | 6/1985 |
| JP | 7155343 A | 6/1995 |
| RU | 1771722 A1 | 10/1992 |
| RU | 1812982 A3 | 4/1993 |
| RU | 1821177 A1 | 6/1993 |
| SE | 8801686 L | 3/1989 |

(56) References Cited

FOREIGN PATENT DOCUMENTS

| | | |
|---|---|---|
| SU | 1667855 A1 | 8/1991 |
| WO | 84/00881 A1 | 3/1984 |
| WO | 95/05792 A1 | 3/1995 |
| WO | 96/21405 A1 | 7/1996 |
| WO | 98/04218 A1 | 2/1998 |
| WO | 98/55055 A1 | 12/1998 |
| WO | 99/05991 A2 | 2/1999 |
| WO | 99/65434 A1 | 12/1999 |
| WO | 00/03665 A1 | 1/2000 |
| WO | 00/74611 A2 | 12/2000 |
| WO | 01/54631 A1 | 8/2001 |
| WO | 01/70147 A2 | 9/2001 |
| WO | 02/26158 A2 | 4/2002 |
| WO | 02/065958 A2 | 8/2002 |
| WO | 02/067825 A2 | 9/2002 |
| WO | 02/080813 A2 | 10/2002 |
| WO | 03/077797 A2 | 9/2003 |
| WO | 03/099173 A1 | 12/2003 |
| WO | 03/099188 A1 | 12/2003 |
| WO | 2005/039444 A2 | 5/2005 |
| WO | 2005/105000 A1 | 11/2005 |
| WO | 2006/012820 A1 | 2/2006 |
| WO | 2010/141960 A2 | 12/2010 |
| WO | 2011/035099 A1 | 3/2011 |
| WO | 2012010309 A1 | 1/2012 |
| WO | 2012/177965 A1 | 12/2012 |
| WO | 2014194998 A1 | 12/2014 |

OTHER PUBLICATIONS

International Search Report from PCT Application No. PCT/US2015/044434, Oct. 8, 2015.
International Search Report from PCT Application No. PCT/US2015/041089, Oct. 5, 2015.
International Search Report from PCT Application No. PCT/US2016/012215, May 23, 2016.
International Search Report from PCT Application No. PCT/US2016/033707, Jul. 29, 2016.
Brochure, "Sometimes Less is More, Harmony P3" Otto Bock, 12 pages. Available at, http://www.ottobock.com/cps/rde/xbcr/ob_es/646A303-EN-01-1001w.pdf, dated 2012.
Information Guide, "Harmony Users Guide Otto Bock, 9 pages, available at http://media.ottobock.com/Prosthetics/Socket-Technologies/Harmony/_Genreal/Files/12072403.1_OB-Harmony-UsersGuide-9-10-12.pdf", dated 2012.
Brochure,"Harmony Certification Course Manual, Original Harmony Pump, 42 pages. Availiable at, http://academy.ottobockus.com/videos/harmony/data/downloads/harmony%20course%20manual%202013.pdf." Dated 2013.
Brochure, Harmony P2 & HD, 2 pages. Available at http://www.ottobock.com/cps/rde/xchg/ob_us_en/hs.xsl/14904.html?id=4641. Dated 2012.
International Search Report from corresponding PCT Application No. PCT/US2013/025849, Jun. 4, 2013.
International Search Report and Written Opinion Regarding Application No. PCT/US2013/038668, Aug. 7, 2013.
Haberman, Louis J., "Silicone-Only Suspension (SOS) with Socket-Loc and the Ring for the Lower Limb", found at, http://www.oandp.org/jpo/library/1995_01_002.asp. Journal of Prosthetics and Orthotics 1995; vol. 7, No. 1, p. 2, 19 pages, dated 2012.
International Search Report and Written Opinion of the International Searching Authority from International Application No. PCT/US2014/019218, mailed May 9, 2014.
Chinese Examination Report from Chinese Application No. 201380022874.0, Aug. 25, 2015.
International Search Report from corresponding International PCT Application No. PCT/US2015/037204, Sep. 25, 2015.
International Search Report from corresponding PCT Application No. PCT/US2016/033915, Jul. 29, 2016.
International Search Report from PCT Application No. PCT/US2016/046967, Oct. 24, 2016.

* cited by examiner

PUMP MECHANISM FOR VACUUM SUSPENSION SYSTEM

TECHNICAL FIELD

The disclosure relates to a pump mechanism for increasing vacuum in a vacuum assisted suspension system.

BACKGROUND

Amputees commonly use prosthetic devices to improve their mobility and associated quality of life. Various types of prostheses exist for replacing the functionality of a missing limb. Transtibial and transfemoral prostheses are effective at helping amputees regain the ability to walk on their own. Various forces cause separation between a prosthetic limb and a residual limb, especially during use. This may happen, for example, during the swing phase of ambulation, when a prosthetic leg is subjected to both gravitational and centrifugal forces. The manner in which an artificial limb is attached to a residual limb determines the control an amputee has over the prosthesis.

Amputees can secure prosthetic devices on their residual limbs by using various vacuum or suction arrangements, whereby the maximum strength of the force holding the prosthesis to the residual limb is a function of the atmospheric pressure. The differential air pressure is routinely referred to as suction or vacuum by those having skill in the art. To maintain the sub-atmospheric pressure created within the distal end of the socket, sealing sleeves or liners have been provided to prevent an influx of air around the distal end of the residual limb. Such liners are provided between the residual limb and the socket to provide for slight compression, and a gripping connection is provided to assist with the suction suspension.

The liner can be rolled onto the residual limb so the liner-covered limb can then be inserted into the socket. The use of conventional liners alone only provides a partial suction fit since they do not form a true air-tight seal with the socket. Some air will slowly enter the socket, especially during the swing phase of the patient's gait and during periods of inactivity.

Conventional vacuum systems have been used to increase the suction within the socket. Such vacuum systems may utilize a valve at a distal end of an otherwise closed socket arranged to receive the distal end portion of a residual limb. These systems work by exhausting air only from the space between the distal end of the residual limb and the distal end of the socket interior as the limb is fully inserted into the socket. Any air that has migrated to areas other than the distal end can remain trapped, and this action affects the optimal pressure differential and diminishes the strength of the suction connection. There is a clear need to provide a way to allow a user to expel air from within any area of the socket.

The use of a valve is intended to allow air to be expelled from the socket in order to maintain at least a slight negative pressure for creating suction against the residual limb. Although the swing phase of the gait cycle will tend to pull the socket off the limb, walking and other weight-bearing activities may push the limb further into the socket. Pushing the limb further into the socket causes the valve to expel air. Conversely, directly pulling the limb out of the socket is prohibited due to the effect of suction.

Using a valve alone may not be an effective or efficient way to expel excess air from within the socket. Many conventional vacuum suspension systems consequently include a vacuum pump to create the desired vacuum effect.

Current vacuum pumps used with prosthetic sockets have several disadvantages, including their size, weight and difficulty of use. For many patients, the time-consuming steps involved with operating the pump combined with the cumbersome placement and unreliability of accurately regulating pressure convinces them to avoid using prostheses entirely.

It can be seen from the foregoing there are many needs for improving on the drawbacks of conventional vacuum suspension systems for attaching to prosthetic sockets. The embodiments of the present disclosure address these aforementioned shortcomings of known prosthetic systems.

SUMMARY

According to various embodiments of the disclosure, a pump mechanism is provided for imparting a quick, easy and reliable way to regulate air differential within a prosthetic socket for adjusting the level of suction. The embodiments of the present disclosure can allow a patient to adjust the desired level of suction suspension on the fly, during use, or when immobile, such as when initially donning a prosthesis.

In an embodiment, a vacuum suspension system includes a pump mechanism operatively connectable to a prosthetic socket. The pump mechanism has a first member and a second member. First and second fluid chambers are located between the first and second members. The second fluid chamber is fluidly separate from the first fluid chamber, and arranged for fluid communication with the socket. An increase in volume of the first fluid chamber mechanically expands the second fluid chamber, which, in turn, creates a vacuum pressure in the second fluid chamber. The resulting vacuum pressure can draw air out of the socket interior and into the pump mechanism.

According to an embodiment, a pressure source is arranged to selectively introduce pressure into the first fluid chamber to increase the volume of the first fluid chamber. Because the first and second fluid chambers are fluidly separate from one another, the pressure source can introduce pressure derived from different sources into the first fluid chamber without interfering with the vacuum pressure generated by the pump mechanism in the second fluid chamber. This advantageously provides a greater degree of freedom of how to activate the pump mechanism. For instance, the pump mechanism can be controlled using pneumonic and/or hydraulic pressure from the pressure source.

Further, because the pump mechanism is operable independent of the pressure level inside of the socket, the pump mechanism can also be placed at virtually any position and is not restricted to a particular location relative to the socket. For instance, the pump mechanism can be located directly on the foot, at the knee, on the socket, or at any other suitable location, avoiding the cumbersome placement of vacuum pumps in the prior art.

Additional features and advantages of embodiments of the present disclosure will be set forth in the description that follows, and in part will be obvious from the description, or may be learned by the practice of such exemplary embodiments. These and other features will become more fully apparent from the following description and appended claims, or may be learned by the practice of such exemplary embodiments as set forth hereinafter.

BRIEF DESCRIPTION OF THE DRAWINGS

To further clarify the above and other advantages and features of the present disclosure, a more particular description of the disclosure will be rendered by reference to specific embodiments illustrated in the drawings. It is appreciated that these drawings depict only typical embodiments of the disclosure and are not to be considered limiting of scope, and are not necessarily drawn to scale. The disclosure will be described and explained with additional specificity and detail through the use of the accompanying drawings.

DETAILED DESCRIPTION

Figure 1:
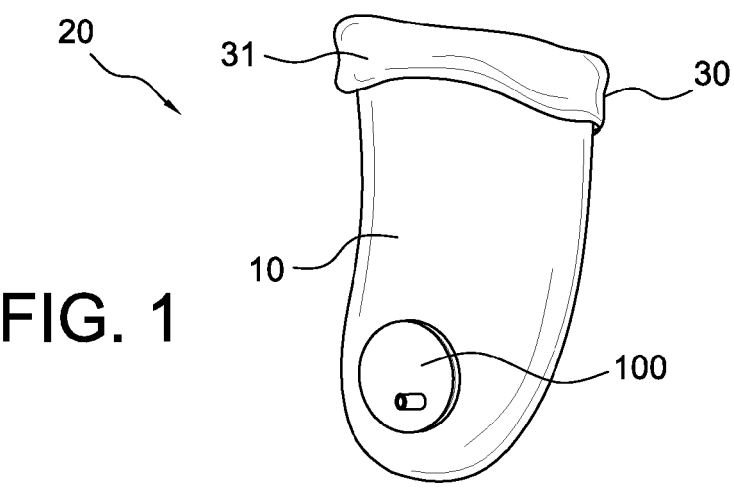
FIG. 1 is a perspective view of a vacuum suspension system secured to a prosthetic socket according to an embodiment of the disclosure.
Figure 2:
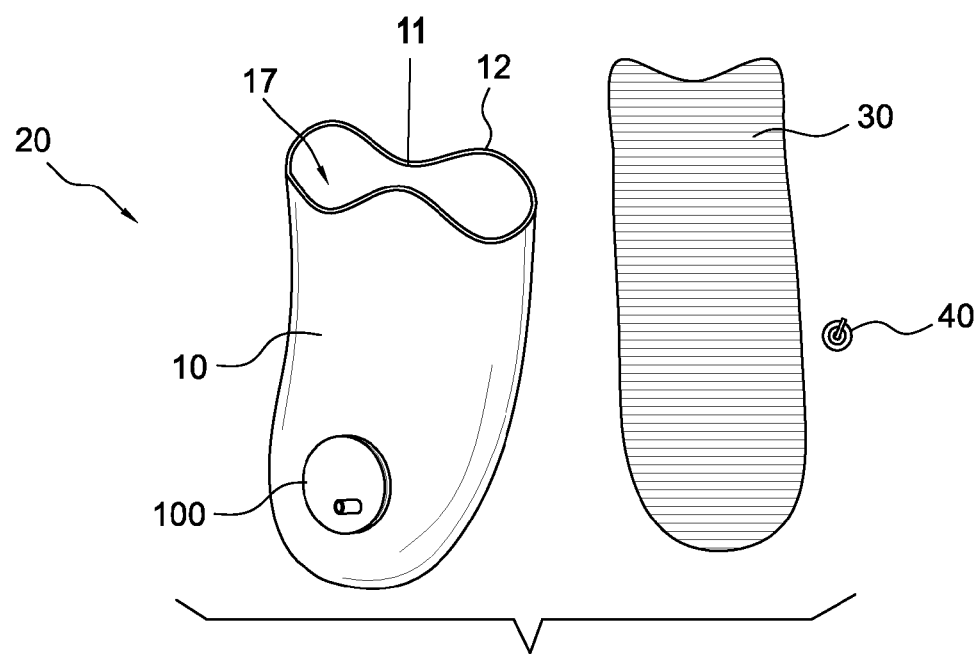
FIG. 2 is an elevational view illustrating individual components of the system shown in FIG. 1.
Figure 3:
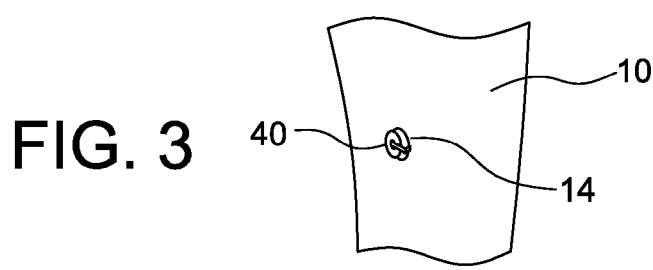
FIG. 3 is a partial schematic view of the prosthetic socket of FIG. 1.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is expressly defined in this disclosure to possess a described meaning, there is no intent to limit the meaning of such term, either expressly or indirectly, beyond its plain or ordinary meaning.

The vacuum suspension system described is configured for use with a prosthetic socket, such as a lower leg prosthesis. It should be remembered, however, that the same concepts and methods described may be similarly used for other prosthetic and/or orthopedic devices and are not limited solely to the anatomical locations discussed. General anatomical terms for the human body may be used for describing particular locations of the elements of the vacuum suspension system in comparison to the human body.

The terms "proximal" and "distal" generally refer to areas on the prosthetic socket that correspond to a location relative to where a residual limb can be inserted. For instance, the proximal end of the socket is its open end where a residual limb is first inserted into. The distal end of the socket is opposite the proximal end and includes at least part of a cavity of the socket arranged to receive a residual limb.

The pump and vacuum suspension system of the present disclosure is described for use with a hard unitary prosthetic socket. This socket defines a shell having a receiving portion for a residual limb and an interior chamber for accommodating the residual limb. The shell is preferably structurally rigid and air impervious. It should be appreciated that many configurations of the socket shell may be used with the vacuum suspension system.

Various embodiments of the pump may be incorporated into many prosthetic appliances, including above and below the knee lower limb prosthetics, and upper limb prosthetics. While the advantages of the pump are discussed with respect to lower limb prostheses, similar advantages can be achieved when the pump applies to upper limb prostheses.

The prosthetic socket of the present disclosure relies on vacuum pressure to ensure a secure connection with a residual limb, while also improving the fit and comfort between the socket and the limb. The differential air pressure caused by using a pump creates a suction effect that helps retain or suspend a residual limb within a prosthetic socket.

To ensure that the suction suspension created by the pump works as intended, a liner may be worn over the residual limb so it is positioned within the socket. Optionally, the liner may include one or more seal elements adapted to engage at least an interior wall of the socket. The area below the seal component can form a vacuum zone within the socket. Besides assisting with suction inside the socket so the residual limb does not fall out, a liner may also be worn to provide cushioning to the limb and to provide a gripping connection to the interior surface of the socket. Using a liner to provide a tight fit for the residual limb within a socket also helps prevent air from entering the socket interior from outside of the socket.

An example of a socket and method for making the same are found in U.S. Pat. No. 5,885,509, granted Mar. 23, 1999, and U.S. Pat. No. 7,105,122, granted Sep. 12, 2006, both incorporated herein by reference. An exemplary liner sleeve for combination with the socket is found in U.S. Pat. No. 8,911,506, granted Dec. 16, 2014, U.S. Pat. No. 9,066,821, granted Jun. 30, 2015, U.S. Pat. No. 9,060,885, granted Jun. 23, 2015, U.S. Pat. No. 9,056,022, granted Jun. 16, 2015, U.S. Pat. No. 6,136,039, granted Oct. 24, 2000, U.S. Pat. No. 6,626,952, granted Sep. 30, 2003, U.S. Pat. No. 6,485,776, granted Nov. 26, 2002, U.S. Pat. No. 6,706,364, granted Mar. 16, 2004, U.S. Pat. No. 7,001,563, granted Feb. 21, 2006, and U.S. Pat. No. 7,118,602, granted Oct. 10, 2006, each of which are incorporated herein by reference in their entirety.

If the liner may not provide a true air-tight seal with the socket, some air will slowly enter the socket interior during use. The presence of additional air within the socket would disrupt the pressure differential between the inside of the socket and the surrounding ambient air outside the socket, thus decreasing the suction and potentially causing the limb to become disengaged from the socket.

It is important to provide a sufficient amount of suction for suspending a prosthesis to a residual limb during ambulation. Air may be drawn into the interior of conventional sockets during the repeating phases of a normal gait cycle. The repetitive motions displayed between the stance and swing phases of walking generate a pumping and pistoning effect within the socket, which draws in air. Even conventional prosthetic sockets with sealing systems sometimes experience some air leaking into the socket interior over a course of use.

When the pressure within the socket reaches atmospheric pressure, the increased volume of air inside will allow the residual limb to move within the socket and potentially separate altogether. Any extraneous movement of the limb within the socket could cause the patient additional medical problems, including chafing of the skin. Moreover, patients who notice a loose connection between the residual limb and the prosthesis may also suffer increased anxiety stemming from their insecurity regarding whether and/or when the prosthesis will fall off their limb.

To combat this problem, the present disclosure provides a pump mechanism for a vacuum suspension system that converts pneumatic or hydraulic pressure into vacuum pressure to expel air from a sealed region between the socket interior and the liner-sheathed residual limb. The negative pressure within this sealed region increases as air is drawn out, correspondingly increasing the suction available to hold the prosthesis to the residual limb.

Using the pump mechanism by itself provides a desired amount of suction within the socket including during ambulation or while motionless. Alternatively, it can supplement the amount of suction produced during ambulation or when the socket is initially donned.

Embodiments of the pump mechanism provide a quick, easy and reliable way to regulate air differential within a prosthetic socket for adjusting the level of suction. As discussed in more detail below, by providing a pump mechanism that can be secured directly on the socket, a patient can adjust the desired level of suction suspension on the fly during use or when immobile, such as when initially donning a prosthesis.

Another advantage of the pump mechanism is that it can utilize pressure (pneumonic or hydraulic) derived from various sources such as bladder placed on the foot or a hand pump mechanism, which allows the pump mechanism to keep a low profile and to be located almost anywhere.

FIGS. 1-4 illustrate a vacuum suspension system 20 including a pump mechanism 100 according to an embodiment. The vacuum suspension system 20 can be operatively connected to a prosthetic socket 10 and the pump mechanism 100 can be in fluid communication with an interior cavity 17 of the socket 10.

The socket 10 is preferably rigid and can be donned over the patient's residual limb. A soft gel-like interface liner 30 can be placed on the residual limb before the limb is inserted into the socket 10. The liner 30 can be preferably fabricated from silicone or other impermeable material. Because of the gel-like qualities of the liner 30, it may need to be rolled onto the limb rather than directly pulled on like a sock. Rolling the liner 30 on the limb in this fashion can ensure that there is only a miniscule amount of air remaining between the limb and the inner surface of the liner 30. The liner 30 is intended to provide a snug fit against the entire circumference of the limb. Providing a tight fit helps stop air from entering the space between the liner and the limb. This type of fit is also important to prevent the liner from being loosened or removed from the limb when tension is applied.

The liner 30 may also provide additional cushioning to the residual limb. The liner may create an air-tight seal for trapping air within the space between the socket interior and the exterior of the liner 30. This can be accomplished by folding a proximal end 31 (shown in FIG. 1) of the liner 30 over the outer rim 12 of the socket 10 at its proximal end. Alternatively, the liner 30 may include one or more seal elements adapted to engage at least an interior surface of the socket wall 11 (shown in FIG. 2) to create an air-tight seal between a distal area of the socket interior and the exterior of the liner 30. Preferably the socket 10 is rigid so the seal formed with the liner 30 is air tight. Partial suction may form between the liner-sheathed limb and the socket 10. Maintaining such partial suction is possible if the liner is properly contoured to the shape of the residual limb.

A total suction fit between the liner-sheathed limb and the socket 10, however, can include using the pump mechanism 100. For instance, the pump mechanism 100 can provide a vacuum for expelling excess air from within the socket interior if the sealing engagement fails between the liner 30 and the socket 10. This can help reduce the likelihood of the residual limb undesirably moving within the socket and/or potentially separating altogether.

The pump mechanism 100 can be located in any suitable location but is shown attached to the socket 10. The pump mechanism 100 can be removably attached to the socket 10 such that it can be easily removed to clean the socket 10 and/or the pump mechanism 100. This also allows the individual parts of the pump mechanism 100 to be easily replaced or repaired if they become damaged.

The pump mechanism 100 may be positioned over an aperture 14 (shown in FIG. 3) defined in the socket wall 11. The aperture 14 extends between an exterior surface of the socket wall 11 to the interior surface of the socket wall 11. The interior surface defines an interior cavity 17, as the socket 10 has a closed distal end and an open proximal end.

Optionally, a fluid regulator or valve 40 can be situated within the aperture 14 to control fluid flow between the interior and the exterior of the socket 10. The valve 40 may be arranged to regulate the air pressure within the socket 10 so an undesirable pressure differential does not adversely affect donning and doffing. The valve can also help maintain a sufficient amount of suction suspension for the prosthesis and regulates the air pressure in the socket 10. The valve can relieve buildup of pressure when the liner-sheathed residual limb is inserted into the socket 10. This aids in preventing a positive internal pressure relative to the ambient air outside of the socket 10 to allow for donning.

The valve 40 preferably may be a one-way valve, also referred to as a check valve. The one-way valve only allows air to be expelled from the socket for maintaining an internal negative air pressure relative to the ambient air pressure outside the socket assisting in sustaining suction. In other embodiments, the valve 40 may be omitted. For instance, the pump mechanism 100 can be directly attached to the aperture 14 and/or in fluid communication with the aperture 14 via a fluid conduit such as a tube or hose.

In order to easily and quickly create sufficient suction suspension, the pump mechanism 100 allows a user to remove any extra air inside of the socket 10. Creating a stronger suction suspension is useful to expel additional air out from the socket 10 before the user even takes a first step or during use. By activating the pump mechanism 100 to expel air from the socket interior, the vacuum suspension system 20 offers an amputee superior control over the level of suction suspension desired.

As discussed in more detail below, the pump mechanism 100 defines a first fluid chamber having a variable volume and a second fluid chamber having a variable volume. The first fluid chamber and the second fluid chamber are separate structures that are fluidly separate from one another such that fluid does not flow between the two fluid chambers.

An activating positive pressure introduced into the first fluid chamber can mechanically expand the second fluid chamber, which, in turn, creates a vacuum pressure in the second fluid chamber. The resulting vacuum pressure can draw air out of the socket interior through a one-way valve in fluid connection with the second fluid chamber and the socket interior. Because the first and second fluid chambers are in fluid isolation from one another, the pump mechanism can utilize pressure derived from different sources in the first fluid chamber without interfering with the vacuum pressure generated in the second fluid chamber. This advantageously provides a greater degree of freedom of how to activate the pump. For instance, the pump mechanism 100 can be controlled with pneumonic and/or hydraulic pressure.

The pump mechanism 100 can also be placed at any position and is not restricted to a particular location. The pump mechanism 100 can be located directly on the foot, at the knee, on the socket, or at any other suitable location, avoiding the cumbersome placement of vacuum pumps in the prior art.

Figure 4:
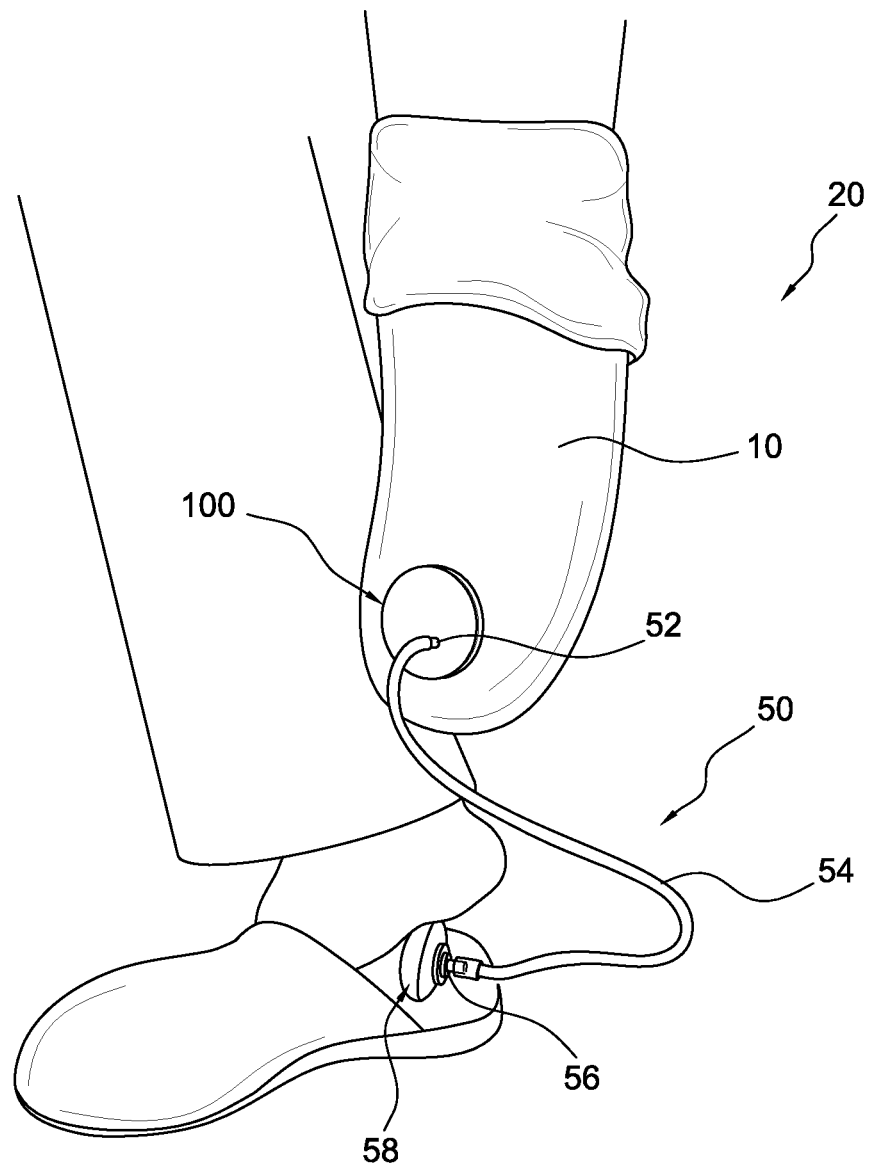
FIG. 4 is an isometric view of the embodiment of FIG. 1 including a pump system.

FIG. 4 shows the pump mechanism 100 operatively connected to a pump system 50. A first connecting portion 52 is located on the pump mechanism 100 to provide fluid engagement between the first fluid chamber of the pump mechanism 100 and a tubular fluid conduit 54. The fluid conduit 54 can be attached at one end to the first connecting portion 52, and at its opposite end to a second connection portion 56 for providing fluid engagement to a pressure source or an actuation pump 58. The actuation pump 58 is shown disposed under the heel of a sound leg but can be placed in a suitable location. For instance, the actuation pump 58 can be located at flexible or moving junctions on the prosthetic side (e.g., between foot plates, within ankle or knee components, or under a prosthetic foot), or within reach of the hand for manual pumping. In other embodiments, the actuation pump 58 may comprise a distal bladder in the socket. The actuation pump 58 can be compressed due to the positive pressure created on it by rocking motion between the bladder and the socket. The actuation pump 58 may be configured to fit in the insole of a shoe, within a foot cover, or in a specially designed pump chamber.

The actuation pump 58 can serve as a manual pump, such that when compressed, activating fluid (e.g., air, water and/or alcohol) inside the actuation pump 58 is expelled through the fluid conduit 54 and into the first fluid chamber of the pump mechanism 100. This action causes the first fluid chamber to mechanically expand, which, in turn, causes a concurrent expansion of the second fluid chamber of the pump.

The increase in volume of the second fluid chamber creates a vacuum effect, which can draw air out of the socket interior through a one-way valve described below in fluid connection with the second fluid chamber and the socket interior. If the system 20 includes a separate valve situated between the pump mechanism 100 and the socket 10 (e.g., the valve 40 on the socket 10), the negative pressure created within the second fluid chamber can release the valve to draw fluid or air out from within the socket interior. If the system 20 does not include a separate valve between the pump mechanism 100 and the socket 10, the negative pressure within the second fluid chamber can draw air directly out from the socket interior via the opening in the socket wall.

When the actuation pump 58 is disengaged, the volume of the actuation pump 58 increases, which, in turn, draws the activating fluid out of the first fluid chamber of the pump mechanism 100 and back into the actuation pump 58, which, in turn, causes the volume of the first fluid chamber to move back towards its initial pre-inflated state. As the first fluid chamber returns to its initial pre-inflated state, the second fluid chamber of the pump mechanism 100 concurrently decreases in volume and the air drawn out from the socket interior into the second fluid chamber is expelled into the atmosphere or another space through another one-way valve.

The actuation pump 58 may also be activated automatically during ambulation. For instance, the actuation pump 58 can be placed underneath the patient's prosthetic foot and/or sound foot so that when pressure is naturally applied to the actuation pump 58 by the patient's weight while walking, the vacuum pumping process occurs.

For instance, the actuation pump 58 may be compressed due to the positive pressure created on it during the heel strike stage of walking, causing the fluid to be transported through the conduit into the first fluid chamber. This would advantageously allow a user to repeatedly pump any excess air out of the socket interior while walking for continuous suction suspension. The actuation pump may be compressed due to the positive pressure created on it during stance.

While the vacuum suspension system is shown including the actuation pump 58, it will be appreciated that in other embodiments the vacuum suspension system 20 can include any mechanism suitable to compress the fluid (e.g., air, water, alcohol) into the first fluid chamber of the pump mechanism 100.

The operation of the actuation pump 58 does not have to depend on the pressure inside of the socket 10, thus the actuation pump 58 can be separate from the pump mechanism 100 and/or the socket 10. This advantageously allows the pump mechanism 100 to be more comfortable, smaller, and lighter in weight than the vacuum pumps in the prior art. For instance, placing the pump mechanism 100 directly on the socket 10 does not make wearing the socket uncomfortable for the user. Securing the pump mechanism 100 directly to the socket also decreases the likelihood that a patient might lose the pump during use.

FIGS. 5-9 illustrate a pump mechanism 200 according to an embodiment. The pump mechanism 200 can include a second member 202 or a base, a first member 204 or housing, and a bladder 218 situated between the base 202 and the housing 204.

Figure 5:
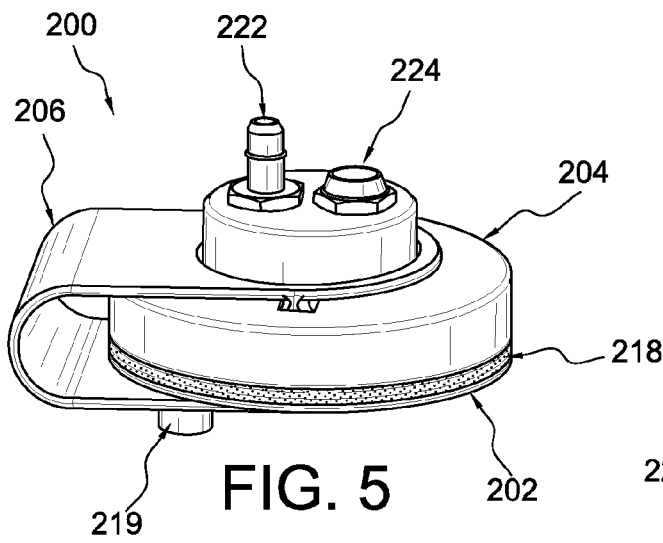
FIG. 5 is an isometric view of a pump mechanism according to an embodiment.
Figure 6:
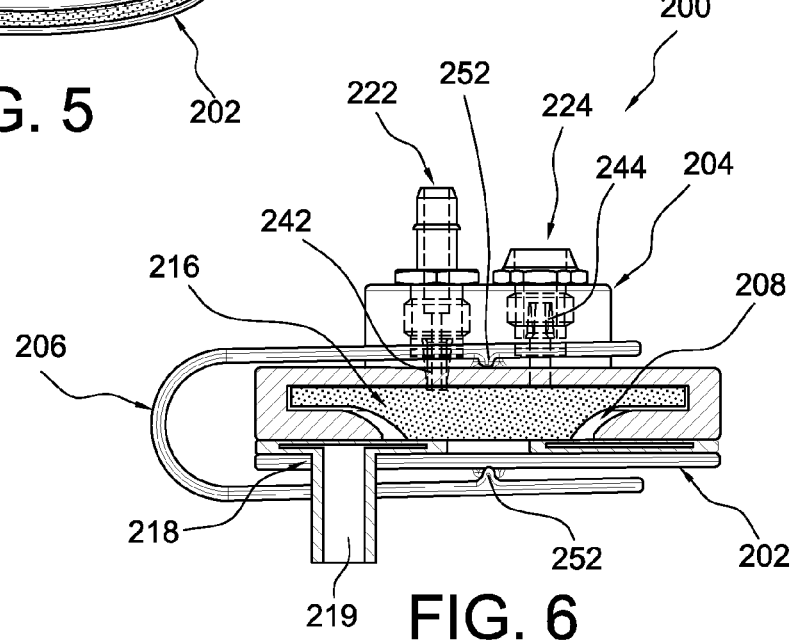
FIG. 6 is a cross-sectional view of the pump mechanism of FIG. 5 in a closed position.
Figure 7:
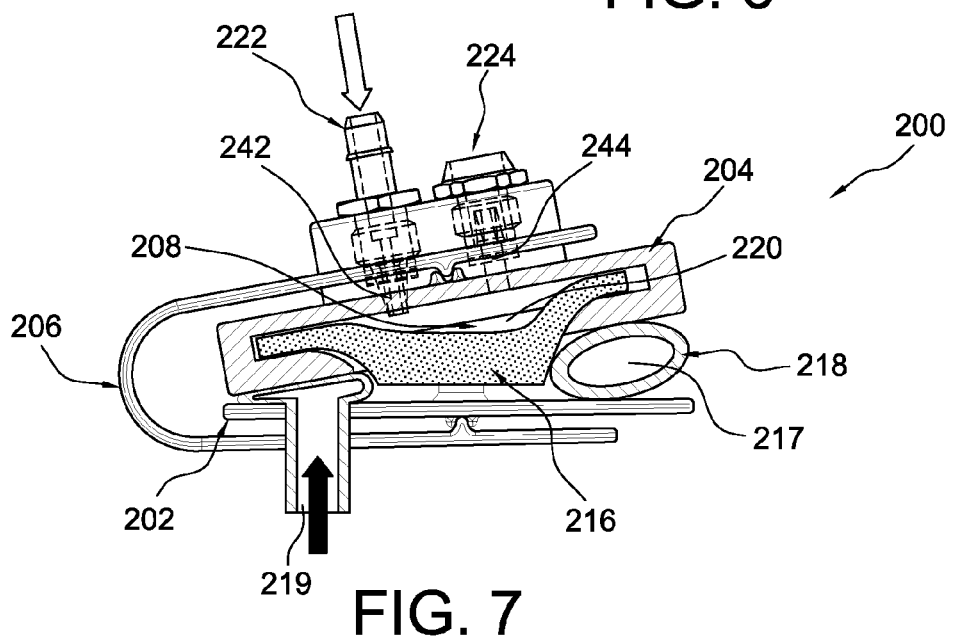
FIG. 7 is a cross-sectional view of the pump mechanism of FIG. 5 in an open position.

Referring now to FIGS. 5-7, the bladder 218 defines a first fluid chamber 217 having a variable volume and is shown to have a generally torus or donut-like shape but may take any form. A connecting portion 219 may be integrally formed on the bladder 218. The connecting portion 219 can provide fluid engagement between the first fluid chamber 217 and an actuation pump or another pressure source, a tubular fluid conduit, and/or a fitting. For instance, a fluid conduit can be attached at one end to the connecting portion 219, and can be attached at its opposite end to the actuation pump.

Inside the pump mechanism 200 is a membrane 216 having a flexible configuration that is operatively connected between the base 202 and the housing 204. The membrane 216 can be situated at least in part within a cavity 208 defined in the bottom of the housing 204. A second fluid chamber 220 has a variable volume defined between the housing 204 and the membrane 216.

The pump mechanism 200 can be movable between a closed position as shown in FIG. 6 and an open position shown in FIG. 7. The pump mechanism 200 may optionally have a resilient member 206 situated thereon which assists in biasing the pump mechanism 200 toward the closed position.

During use, a pressure source (e.g., a pressure activated pump, a mechanical pump, or an electric pump) can move the pump mechanism 200 from the closed position to the open position. The pressure source (e.g., the actuation pump 58 shown in FIG. 4) can compress and force fluid such as air, water, gel, alcohol, or another suitable fluid into the first fluid chamber 217 defined by the bladder 218. This action can cause the volume of the first fluid chamber 217 to increase, which, in turn, causes the base 202 and the housing 204 to mechanically separate. In an embodiment, when the buildup of pressure inside of the first fluid chamber 217 exceeds the biasing force of the resilient member 206, the pressure can expand the bladder 218 so that the base 202 and the housing 204 mechanically separate, activating the pump mechanism 200.

The separation of the base 202 and the housing 204 causes a portion of the membrane 216 to separate or pull away from the housing 204 and increase the volume of the second fluid chamber 220 defined by the space created between the membrane 216 and an interior surface of the housing 204 within the cavity 208. The volume increase in the second fluid chamber 220 creates a vacuum effect, which can draw air out of the interior cavity of a socket through an inlet valve assembly 222 in fluid connection with the second fluid chamber 220 and the interior cavity. When the pressure source is disengaged, the pump mechanism 200 can return to the closed position. The bladder 218 can naturally or elastically return to its pre-inflated state such that fluid in the first fluid chamber 217 is returned to the pressure source from the first fluid chamber 217. Optionally, the biasing force of the resilient member 206 can at least in part return the bladder 218 to its pre-inflated or a zero or near zero volume.

As the bladder 218 returns to its initial pre-inflated state, the base 202 and the housing 204 move back together, this, in turn, decreases the volume of the second fluid chamber 220. As the volume of the second fluid chamber 220 decreases, the air of fluid drawn out from the socket interior into the second fluid chamber 220 can be expelled to atmosphere or another space through an outlet valve assembly 224 in fluid connection with the second fluid chamber 220. In the closed position, the first fluid chamber 217 and/or the second fluid chamber 220 can have a zero or near zero volume.

The pump mechanism 200 advantageously offers an amputee superior control over the level of suction desired because air can be drawn out of the socket interior whenever an activating pressure is introduced into the first fluid chamber 217 of the pump mechanism, consequently increasing the vacuum within the socket 10. Further, the first and second fluid chambers are fluidly separate from one another such that fluid does not flow between the first and second fluid chambers. This advantageously helps to reduce air resistance in the fluid chamber in fluid connection with the socket interior and allows for a variety of ways to generate a vacuum at the socket-liner interface. For instance, the first fluid chamber 217 of the pump mechanism 200 can be arranged such that the pressure mechanism inside of the first fluid chamber 217 (e.g., water) is different than the pressure mechanism inside of the second fluid chamber 220 (e.g., air).

The pump mechanism 200 can also automatically return to the closed position when the activating pressure is disengaged, leaving the pump mechanism 200 ready for another vacuum pumping cycle.

Figure 8:
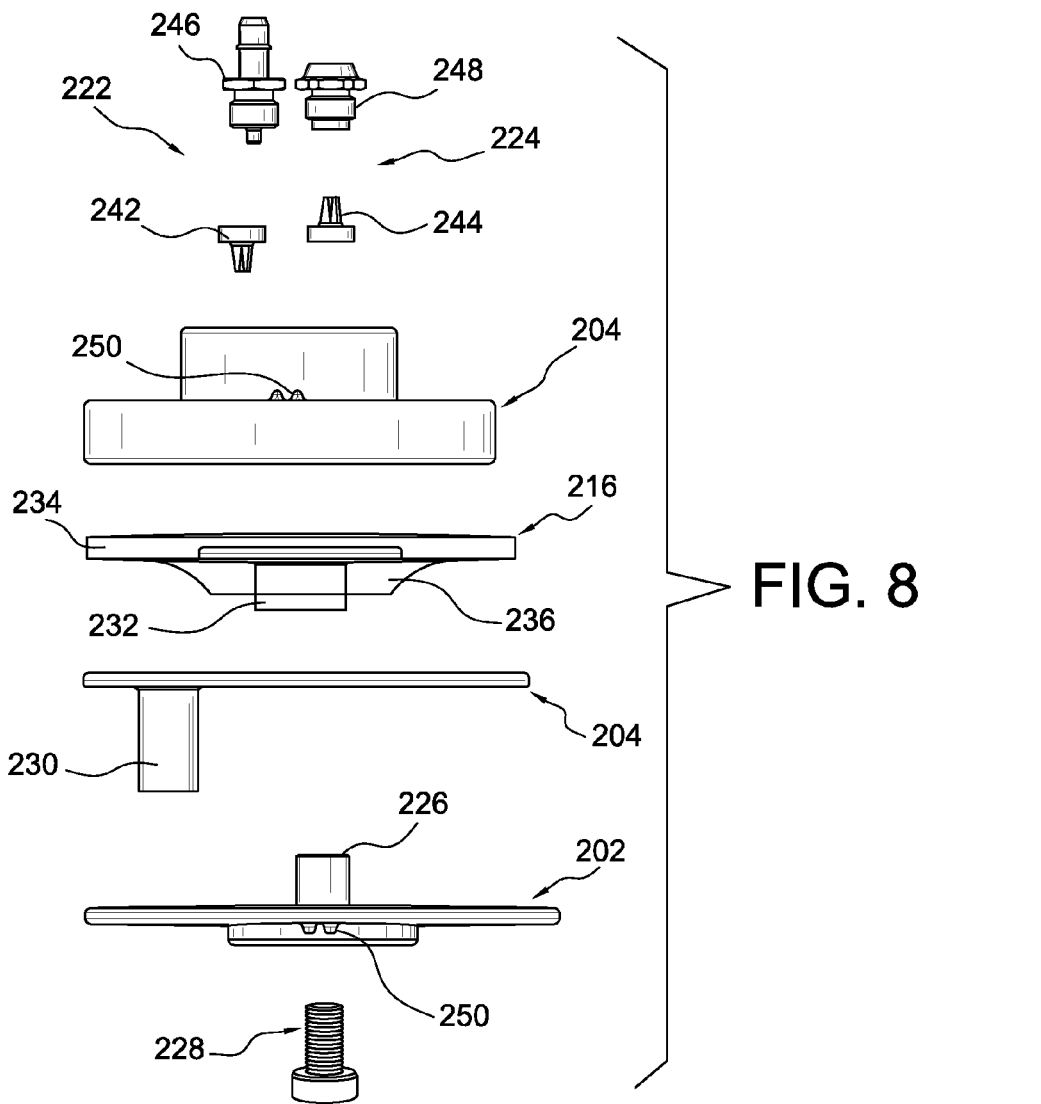
FIG. 8 is an exploded view of the pump mechanism of FIG. 5.
Figure 9:
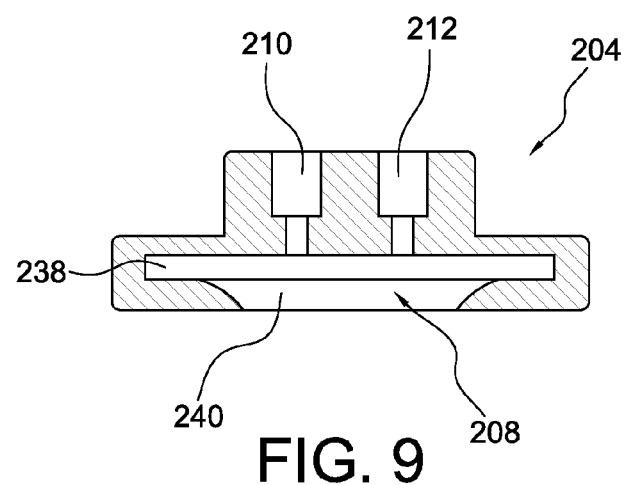
FIG. 9 is a cross-sectional view of the housing shown in FIG. 5.

The construction of the pump mechanism 200 will now be discussed in greater detail in association with FIGS. 8 and 9.

The housing 204 can include an upper section adapted to provide a support surface for the resilient member 206 and a lower section adapted to extend through a hole formed in the resilient member 206. The lower section can be smaller than the upper section. While the housing 204 is shown to have a generally cylindrical configuration, the housing 204 may take any form including any polygonal prism. A variety of suitable material, including different metals, plastics and/or resins, may produce the housing 204.

The housing 204 and the base 202 can include one or more locking features 250 (best shown in FIG. 8) and the resilient member 206 can include corresponding detents or catches 252 (best shown in FIG. 6). The locking features 250 can engage the detents 252 of the resilient member 206 when the resilient member 206 is loaded on the pump mechanism 100 so that the resilient member 206 secures over the housing 204 and the base 202 is at least in part locked thereon.

The cavity 208 of the housing 204 can include an undercut annular groove 238 and a conical portion 240 tapering from the annular groove 238 toward the bottom of the housing 204. The housing 204 can define first port 210 and second port 212, with both the first port 210 and the second port 220 extending axially between an exterior surface of the housing 204 and the second fluid chamber 220. The first and second ports 210, 212 can include a counter-bore section in which the inlet valve assembly 222 and the outlet valve assembly 224 can be respectively situated.

The inlet valve assembly 222 can include an inlet valve 242 to control fluid flow between the socket interior and the second fluid chamber 220. The outlet valve assembly 224 can include an outlet valve 244 to control fluid flow between the second fluid chamber 220 and the atmosphere or another space. The inlet valve 242 and/or outlet valve 244 may comprise a one-way valve, also referred to as a check valve. A preferred type of one-way valve used with the pump mechanism 200 is a duckbill valve. It should be appreciated, however, that other types of one-way valves are possible. The inlet valve 242 can be adapted to only allow fluid or air to be expelled from the socket and into the second fluid chamber 220 for maintaining an internal negative air pressure relative to the ambient air pressure outside of the socket. The inlet valve 242 can prevent fluid in the second fluid chamber 220 from returning to the socket. The outlet valve 244 can be adapted to only allow air be released from the second fluid chamber 220 and into the atmosphere or another space. This advantageously allows the vacuum pressure to be maintained through unidirectional flow of the air through the second fluid chamber 220.

The inlet valve assembly 222 can include a male fitting 246 for connecting the inlet valve assembly 222 to a hose, another fitting, and/or the aperture 14 (shown in FIG. 3) in the socket wall. The outlet valve assembly 224 can include a female fitting 248 for connecting the outlet valve assembly 224 to a tube or expelling air into the atmosphere or another space from the second fluid chamber 220. It will be appreciated that the fittings may exhibit any suitable configuration and/or may be omitted.

The inlet valve assembly 222 can be in fluid communication with the socket interior directly through the aperture 14 (shown in FIG. 14) in the socket wall. The inlet valve assembly 222 can be in fluid communication with the socket interior via a tubular fluid conduit (e.g., the fluid conduit 54). For example, the fluid conduit can be attached at one end to the inlet valve assembly 222 and at its opposite end to the valve 40. This can allow pressure to be isolated in the fluid conduit between the pump mechanism 200 and the socket interior. When the pump mechanism 200 is in fluid communication with the socket interior via a fluid conduit, the pump mechanism 200 can be located anywhere including directly on the foot or at the knee (e.g., in trans-fibular amputees).

The base 202 can be located below or generally opposite the housing 204. The base 202 can have a disc-like configuration including a hollow generally cylindrical stem 226 adapted for receiving a fastener 228 to fasten the base 202 to the membrane 216. Similar to the housing 204, a variety of suitable materials may produce the base 202. Further, while the base 202 is shown to have a disc-like shape, the base 202 may have any form. The housing 204 and the base 202 in this embodiment are shown to be formed as two pieces. However, the housing 204 and the base 202 can be formed of a single continuous member or as any suitable number of pieces.

The stem 226 of the base 202 can be sized and configured to extend through a central opening defined by the bladder 218. The connecting portion 219 of the bladder 218 can extend through an aperture in the base 202. Such an arrangement can help maintain the position of the bladder 218 between the base 202 and the housing 204 as the bladder 218 expands and deflates.

The membrane 216 can exhibit any suitable shape. The membrane 216 can comprise an elastomeric material, a synthetic rubber, a fluoropolymer elastomer, combinations thereof, and/or other suitable material. The membrane 216 can include a body 236 arranged to be seated in the conical portion 240 of the cavity 208 and an outer edge portion 234 arranged to be received in the annular groove 238 of the cavity 208.

An insert 232 can be disposed within the membrane 216 that is configured to threadedly engage with the fastener 228 extending through the stem 226 of the base 202. When the base 202 and the housing 204 separate, the insert 232 can allow the bottom of the membrane 216 to be generally fixed relative to the base 202 while top of the membrane 216 can use at least in part its elastic material properties and its shape to deform, bend, and/or flex inside of the cavity 208 to vary and/or form the second fluid chamber 220.

The engagement between the membrane 216 and the housing 204 inside of the cavity 208 can form a seal to inhibit fluid communication between the second fluid chamber 220 and the area outside of the second fluid chamber 220. As the base 202 and the housing 204 separate, the conical body 236 of the membrane 216 can wedge itself in the conical portion 240 of the cavity 208. This can advantageously improve the seal of the second fluid chamber 220 to help maintain a vacuum pressure in the second fluid chamber 220 as desired. The second fluid chamber 220 may have a variety of shapes depending at least in part on the shape of the cavity 208.

The resilient member 206 can comprise a generally u-shaped member. The resilient member 206 can be selected based on one or more properties (e.g., stiffness) to achieve a desired biasing force on the pump mechanism 200. While the resilient member 206 is described as a generally u-shaped member, it will be appreciated that the resilient member 206 can comprise any suitable member, such as, for example, a torsion spring, a torsion bar, or any other suitable member.

Figure 10:
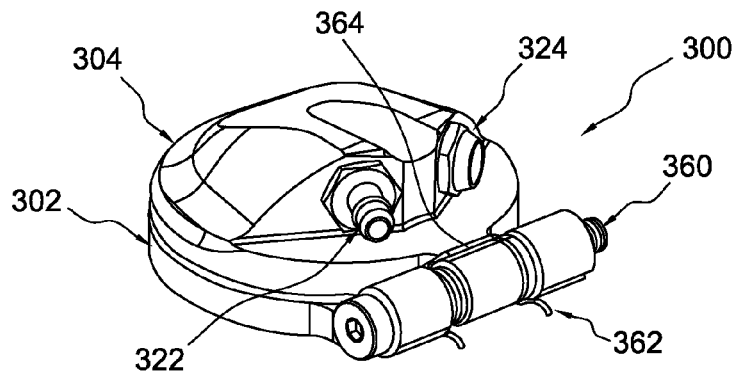
FIG. 10 is an isometric view of a pump mechanism according to another embodiment.
Figure 11:
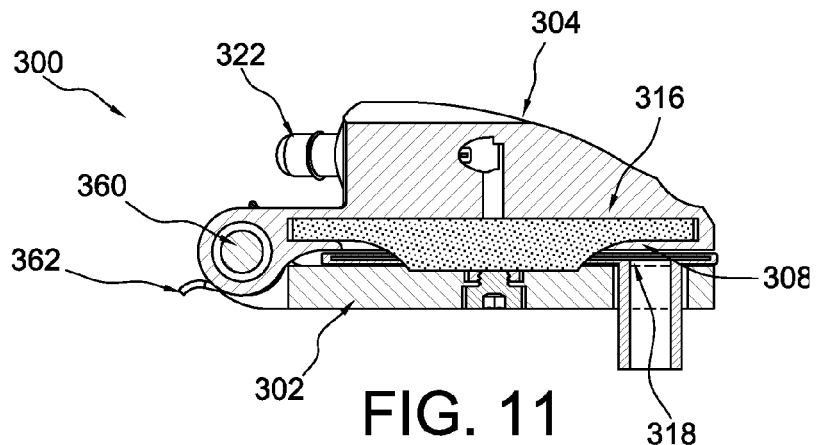
FIG. 11 is a cross-sectional view of the pump mechanism of FIG. 10 in a closed position.
Figure 12:
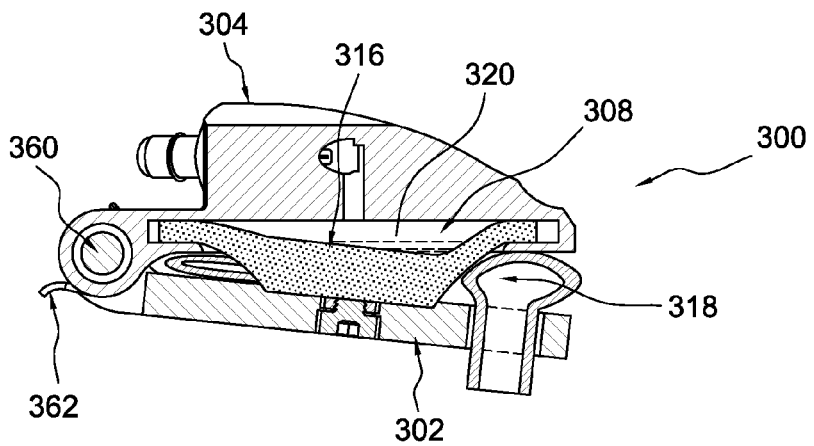
FIG. 12 is a cross-sectional view of the pump mechanism of FIG. 10 is an open position.

FIGS. 10-12 illustrate a pump mechanism 300 according to another embodiment. As seen, the pump mechanism 300 includes an inlet valve assembly 322 and an outlet valve assembly 324 extending radially through ports defined by a first member or housing 304. A second member or base 302 can be pivotally connected to the housing 304 via a retaining pin 360 extending through retaining pin holes in the housing 304 and the base 302. The base 302 can be fixedly attached to the retaining pin 360 such that the base 302 and the retaining pin 360 rotate together. Alternatively, the base 302 can be rotatably attached to the retaining pin 360 such that the base 302 rotates relative to the retaining pin 360. The retaining pin 360 can be integral to the base 302 or the retaining pin 360 can be separate from the base 302.

The base 302 is rotatable about an axis extending through the retaining pin 360 to move the pump mechanism 300 between a closed position shown in FIG. 11 and an open position shown in FIG. 12. In the open position, the base 302 is rotated away from the housing 304, thus allowing air to be drawn out of the socket interior and into a second fluid chamber 320 defined by the space created between the membrane 316 and the interior surface of the receiving cavity 308. Similar to the pump mechanism 200, an activating positive pressure introduced into a bladder 318 can move the pump mechanism 300 from the closed position to the open position.

The base 302 can be biased toward the closed position by a torsion spring 362 loaded on the retaining pin 360. A portion 364 of the torsion spring 362 can engage the top surface of the housing 304 to at least in part transfer stored mechanical energy from the torsion spring 362 to the base 302 and/or the housing 304. The stored mechanical energy in the torsion spring 362 can force the base 302 to the closed position. In the closed position, the second fluid chamber 320 can have a zero or near zero volume.

Figure 13:
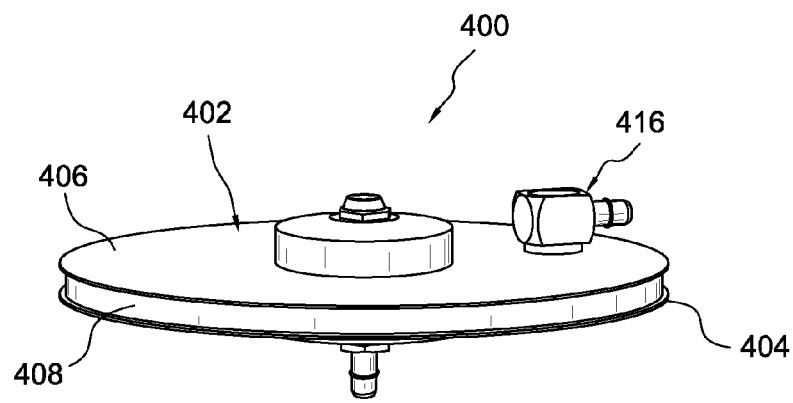
FIG. 13 is an isometric view of a pump mechanism according to another embodiment.
Figure 14:
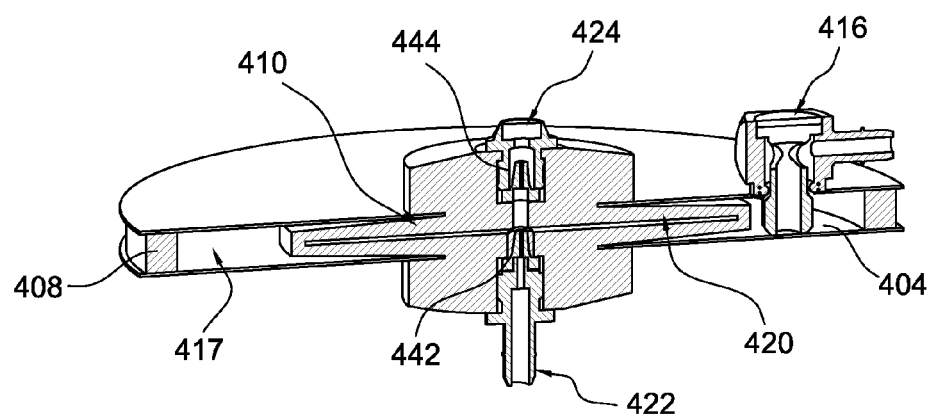
FIG. 14 is a cross-sectional view of the pump mechanism of FIG. 13.

FIGS. 13 and 14 illustrate a pump mechanism 400 according to another embodiment. The pump mechanism 400 includes a first structure 402 comprising a first member or bottom plate 404, a second member or top plate 406, and a flexible seal 408 extending around the perimeter and connecting the plates 404, 406 together. A first fluid chamber 417 is defined between the bottom and top plates 404, 406. The plates 404, 406 can be flexible and can comprise thin metal, thin plastic, thin resin, or any other suitable material. The seal 408 can comprise rubber, glue, or any other suitable material. The first structure 402 can include a valve assembly 416 adapted to control fluid flow between the first fluid chamber 417 and a pump or other pressure source.

Inside of the first structure 402 is a second structure 410 connected to the top plate 406 and the bottom plate 404. The second structure 410 can comprise a clam-type structure including a pair of elastomeric disks facing each other. Each disk can have a suction cup-like shape. The second structure 410 can define a second fluid chamber 420 formed between the elastomeric disks. The second structure 410 can include an inlet valve assembly 422 received in a first port and an outlet valve assembly 424 received in a second port that are independent from the valve assembly 416 incorporated in the first structure 402. The inlet valve assembly 422 can be adapted to control fluid flow between the socket interior and the second fluid chamber 420 and the outlet valve assembly 424 can be adapted to control fluid flow between the second fluid chamber 420 and the atmosphere or another space. The inlet valve assembly 422 and the outlet valve assembly 424 may include a one-way valve or check valve 442, 444, respectively, to maintain unidirectional air flow through the second fluid chamber 420.

It will be appreciated that the embodiments of the pump mechanism are to be regarded as exemplary only. For example, while the membrane is shown comprising a disc-like member, in other embodiments, the membrane may comprise a Belleville washer, a membrane having a flexible and rigid section, a diaphragm valve, or any other suitable sealing element. While embodiments of the pump mechanism are described in use with the vacuum suspension system 20, other vacuum suspension systems are possible. Some example vacuum suspension systems are found in U.S. patent application Ser. No. 13/766,086, filed on Feb. 13, 2013, and Ser. No. 14/192,949, filed on Feb. 28, 2014, both incorporated herein by reference. In other embodiments, the pump mechanism can include three, four, or any other suitable number of fluid chambers.

It should also be appreciated that many variations of the bladder having different shapes and/or sizes can be used for separating the first and second members. Although such variations may differ in form, they perform substantially similar functions. In other embodiments, the inlet valve and/or the outlet valve can comprise an umbrella valve or other suitable valve. In yet other embodiments, the force utilized to separate the first and second members can be a mechanical or magnetic force from a linear actuator, magnets, or any other suitable source. In yet other embodiments, the inlet valve assembly and the outlet valve assembly may comprise a single assembly including a single valve.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open-ended and have the same meaning as the word "comprising" and variants thereof (e.g., "comprise" and "comprises").

The invention claimed is:

1. A vacuum suspension system comprising:
   a pump mechanism including:
      a first member;
      a second member;
      a bladder disposed between the first and second members and defining a first fluid chamber located between the first and second members;
      a second fluid chamber located between the first and second members, the second fluid chamber fluidly separate from the first fluid chamber, wherein an increase in volume of the first fluid chamber mechanically expands the second fluid chamber to create a vacuum pressure in the second fluid chamber; and
   a pressure source fluidly connected to the bladder and separate from the pump mechanism, the pressure source arranged to selectively compress and force fluid into the first fluid chamber to increase the volume of the first fluid chamber.

2. The system of claim 1, wherein the volume increase in the first fluid chamber mechanically separates the first and second members of the pump mechanism to create the vacuum pressure in the second fluid chamber.

3. The system of claim 1, further comprising a membrane having an outer edge portion secured to the first member of the pump mechanism, the second fluid chamber having a volume defined between the first member of the pump mechanism and the membrane.

4. The system of claim 3, wherein the membrane deforms to vary the volume of the second fluid chamber.

5. The system of claim 3, wherein the increase of volume in the first fluid chamber pulls the first member of the pump mechanism and a portion of the membrane apart to increase the volume of the second fluid chamber.

6. The system of claim 3, wherein the first member of the pump mechanism comprises a housing defining first and second ports, the second fluid chamber being in fluid communication with the first and second ports.

7. The system of claim 6, further comprising a connector attached to a portion of the membrane opposite the first member of the pump mechanism.

8. The system of claim 7, wherein the second member of the pump mechanism comprises a base member situated under the housing and connected to the connector.

9. The system of claim 8, further comprising a bladder situated between the housing and the base member, the bladder having a torus configuration defining a center opening, the connector extending through the center opening of the bladder.

10. The system of claim 1, further comprising a resilient member engaging at least one of the first and second members of the pump mechanism, and arranged to bias the second fluid chamber toward a zero or near zero volume.

11. The system of claim 10, wherein the resilient member is arranged to bias the first fluid chamber toward a zero or near zero volume.

12. A prosthetic system comprising:
   a pump mechanism operatively connectable to a prosthetic foot, the pump mechanism including:
      a housing defining first and second ports;
      a membrane having an outer edge portion secured to the housing;
      a base member disposed below the membrane;
      a bladder disposed between the housing and the base member;
      a first fluid chamber with a volume defined by the bladder;
      a second fluid chamber with a volume defined between the housing and a first side of the membrane, the second fluid chamber fluidly separate from the first fluid chamber and in fluid communication with the first and second ports,
      wherein an increase in volume of the first fluid chamber mechanically expands the second fluid chamber to create a vacuum pressure in the second fluid chamber.

13. The system of claim 12, further comprising a connector attached to a second side of the membrane opposite the first side of the membrane, the connector connecting the membrane to the base member.

14. A vacuum suspension system comprising:
   a pump mechanism including:
      a first member;
      a second member;
      a bladder disposed between the first and second members and defining a first fluid chamber located between the first and second members;
      a second fluid chamber located between the first and second members, the second fluid chamber fluidly separate from the first fluid chamber, wherein an increase in volume of the first fluid chamber mechanically expands the second fluid chamber to create a vacuum pressure in the second fluid chamber; and
   a pressure source fluidly connected to the bladder and separate from the pump mechanism, the pressure source arranged to selectively compress and force fluid into the first fluid chamber to increase the volume of the first fluid chamber, wherein the volume increase in the first fluid chamber mechanically separates the first and second members of the pump mechanism to create the vacuum pressure in the second fluid chamber.

15. A vacuum suspension system comprising:

a pump mechanism including:
- a housing defining first and second ports;
- a base member situated under the housing;
- a membrane having an outer edge portion secured to the housing;
- a connector attached to a portion of the membrane opposite the housing;
- a bladder situated between the housing and the base member, the bladder having a torus configuration defining a center opening, the connector extending through the center opening of the bladder;
- a first fluid chamber located between the housing and the base member;
- a second fluid chamber having a volume defined between the housing and the membrane, the second fluid chamber fluidly separate from the first fluid chamber and in fluid communication with the first and second ports, wherein an increase in volume of the first fluid chamber mechanically expands the second fluid chamber to create a vacuum pressure in the second fluid chamber.

\* \* \* \* \*